Sept. 4, 1962 H. C. SWIM Plant Pat. 2,169
CAMELLIA PLANT
Filed Oct. 9, 1961
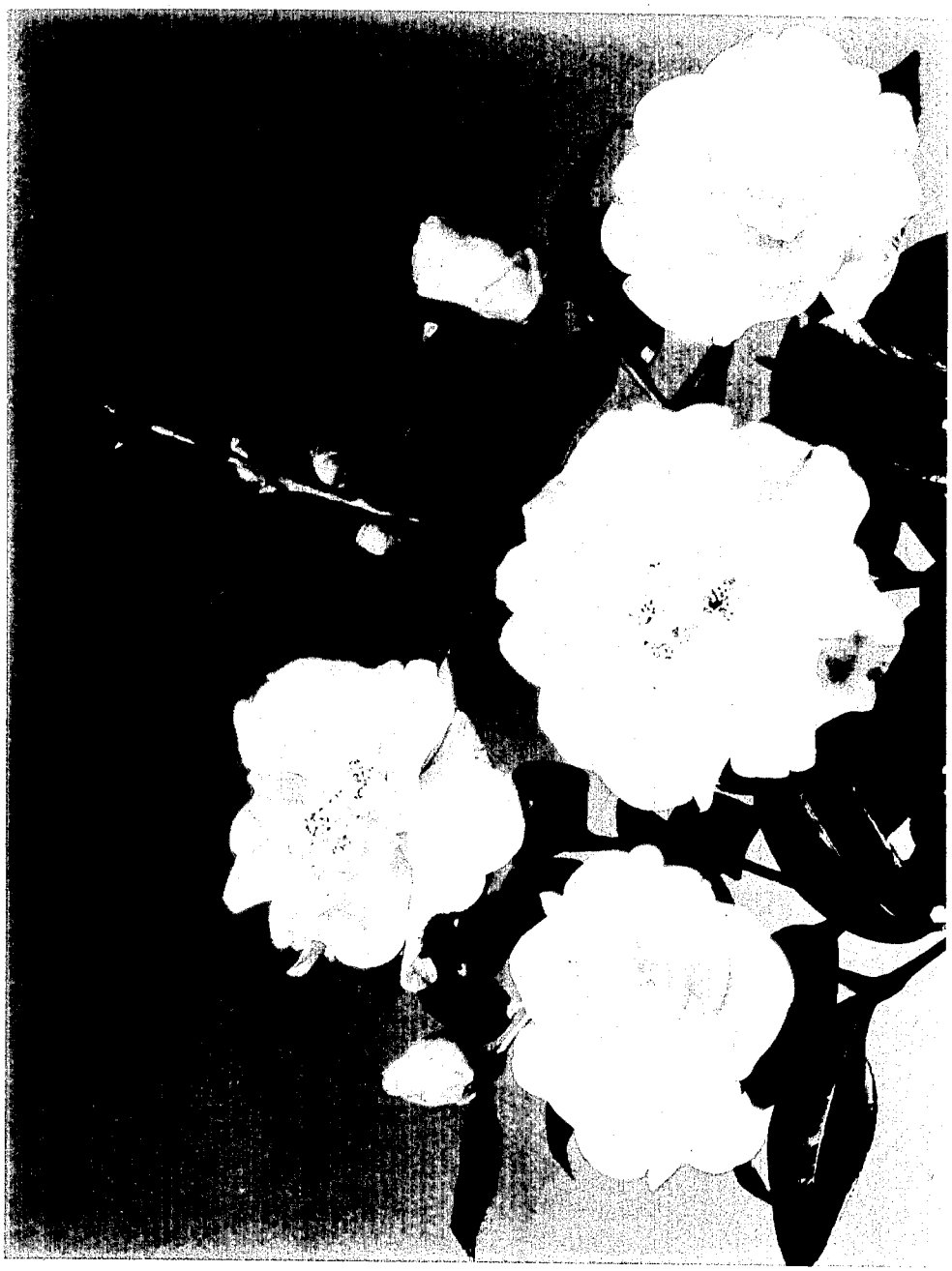
Inventor.
H. C. Swim
By: Robb & Robb
Attorneys.

United States Patent Office

Plant Pat. 2,169
Patented Sept. 4, 1962

2,169
CAMELLIA PLANT

Herbert C. Swim, Ontario, Calif., assignor to Armstrong Nurseries, Inc., Ontario, Calif., a corporation of California Filed Oct. 9, 1961, Ser. No. 144,014
1 Claim. (Cl. 47—60)

The present invention relates to a new and distinct variety of Camellia plant which was originated by me by crossing an unnamed and unpatented variety of the species *Camellia saluenensis* with the *Camellia japonica* variety known as "Princess Baciocchi" (unpatented), the latter being the pollen parent, and the unnamed variety being the seed parent.

The unnamed variety aforesaid is characterized by a more or less semi-spreading to spreading habit of plant growth, with the plant being of compact and bushy form which is well branched and bears very small leaves. This variety is very floriferous, and the flowers are about 4 to 5 cm. in width, single in form, with 6 or 7 petals, and the flowers are a very pale pink or near white in color.

The other parent variety, "Princess Baciocchi" is characterized by an upright-spreading and vigorous plant habit, with the plant having attractive, glossy, large leaves of dark green color and being from near round to oblong shape. The flowers are quite double and from about 12 to 15 cm. wide, with a height corresponding to approximately half their width, when fully expanded, said flowers being quite irregular in form, with the petals intermixed with the stamens and often covering the stamens to a great extent. The flowers are red in color in the case of this parent variety.

The general objective of the breeding of these parents, as referred to above, was to produce an improved Camellia variety which combines the floriferousness and the precocious blooming habit, as well as other good features of the unnamed parent, with the large, double flowers, and the large and attractive foliage characteristics of the variety "Princess Baciocchi."

This objective was largely achieved, along with other desirable improvements, as evidenced by the following unique combination of characteristics which are outstanding in my new Camellia variety and which distinguish it from its parents, as well as from all other varieties of which I am aware:

(1) A vigorous, upright and rather open plant habit, combined with dark green glossy foliage of from small to medium size;

(2) A blooming period between mid-season to late, with the blooming season being approximately two months or more long;

(3) A precocious blooming habit, with the plants blooming well while still young and quite small;

(4) A very floriferous habit, with the flowers borne laterally on most shoots, as well as terminally;

(5) Semi-double flowers having from 12 to 14 petals, plus 1 to 3 petaloids, with the flowers being open in form and varying from a rather formal, open-centered form to more often a very graceful, irregular and high-centered form, with several petals or petaloids intermixed with and partially covering the stamens in an attractive manner;

(6) An attractive and distinctive light pink general color tonality of the flowers corresponding to near Solferino Purple; and (7) A clean flower dropping habit, as evidenced by the fact that the old flowers drop cleanly as entire flowers.

As compared with its unnamed seed parent, the foliage of my new variety is considerably larger, and the flowers are larger, more double and darker pink in color than those of this parent.

As compared with its pollen parent, "Princess Baciocchi," the new variety is more open in plant habit, the foliage is smaller, it is more precocious in blooming, the flowers are semi-double in contrast to the considerably more double flowers of this parent, and the flowers are distinctly different in color, being near Solferino Purple, as compared with the red color of the flowers of this parent.

Asexual reproduction of my new variety by both grafting and cuttings, as performed at Ontario, California, shows that the foregoing characteristics and distinctions come true to form in my new Camellia and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway") as indicated:

Type: Ornamental; flowering evergreen shrub; for general landscape use and for cut flowers.
Class: $F_1$ hybrid of *C. saluenensis* × *C. japonica.*
Breeding: Seedling.

*Seed parent.*—An unnamed variety of *Camellia saluensis.*
*Pollen parent.*—"Princess Baciocchi."

Propagation: Holds its distinguishing characteristics through succeeding propagations by both grafting and cuttings.

*Plant*

Growth:

*Habit.*—Upright; moderately branched; somewhat open.
*Vigor.*—Medium.
*New stems.*—Medium caliper; glabrous. Color—near Absinthe Green, Plate XXXI (Ridgway).
*Older stems.*—Glabrous; bark becomes fissured and scurfy. Color—between Russet, Plate XV (Ridgway) and Cinnamon Brown, Plate XV (Ridgway).
*Mature branches.*—Rough and scurfy when a year or two old but becoming more smooth as original bark is sloughed off. Color—between Drab-Gray, Plate XLVI (Ridgway) and Light Grayish Olive, Plate XLVI (Ridgway).

Leaves:

*Habit.*—Moderately abundant.
*Texture.*—Leathery.
*Size.*—From small to medium. Width—from 2½ to 3½ cm. Length—from 5 to 8 cm.
*Petiole.*—Medium caliper; from 3 to 8 mm. long; with shallow groove along upper surface; glabrous, except for some pubescence along margins of groove.
*Shape.*—Oval. Apex—usually acute. Base—usual-obtuse. Margin—simply serrate, except lower ¼ toward base is usually entire.
*Upper surface.*—Glossy. Color: mature leaves—between Cossack Green, Plate VI (Ridgway) and Empire Green, Plate XXXII (Ridgway); young leaves—near Deep Dull Yellow-Green (1), Plate XXXII (Ridgway). Veins—lighter in color.
*Lower surface.*—Glossy. Color: mature leaves—near Chromium Green, Plate XXXII (Ridgway);

young leaves—near Absinthe Green, Plate XXXI (Ridgway). Veins—darker in color.

*Flower*

Flowers borne: Sessile; terminal or axillary; mostly single, but sometimes double when terminal.

Quantity of bloom: Abundant.

Time of bloom: One season; usually from mid-February to mid-April at Ontario, California.

Fragrance: None.

Bud:

*Size (before calyx breaks).*—Medium.

*Form (before calyx breaks).*—Usually ovoid.

*Sepals.*—Numerous; usually from 6 to 10 in number; increasing in size from the outermost which are nearly round to the innermost which are broadly obovate. Outside surface—pubescent; color—between Rainette Green, Plate XXXI (Ridgway) and Lime Green, Plate XXXI (Ridgway). Inside surface—glabrous; color — near Chrysolite Green, Plate XXXI (Ridgway).

*Opening.*—Opens up well.

Bloom:

*Size (when fully open).*—Medium; averages from 11 to 14 cm.

*Petalage.*—Semi-double; usually from 12 to 14 petals, sometimes with 2 or 3 petaloids; outermost petal usually reduced in size and is more a sepal than a petal.

*Form.*—Newly opened flower somewhat cupped at first, becoming more bell-shaped, and at maturity varying from a rather formal, semi-double, open-centered form to more often a high-centered, gracefully irregular form with several petals intermixed with and often partially covering the stamens.

*Petals.*—Thickness — moderate. Surfaces — satiny, both inside and outside. Shape—somewhat irregular, with outside petals usually broadly obovate, and inside petals usually from broadly oval to round.

*Color.*—Newly opened flower: Outer petals—Outside surface—near Solferino Purple, Plate 26/3, page 26 (Wilson), with veins of petals near Solferino Purple, Plate 26/1, page 26 (Wilson); inside surface—near Solferino Purple, Plate 26/3, page 26 (Wilson), with veins of petals near Solferino Purple, Plate 26/1, page 26 (Wilson). Inner petals—outside surface—near Solferino Purple, Plate 26/3, page 26 (Wilson), with veins of petals near Solferino Purple, Plate 26/1, page 26 (Wilson); inside surface—near Solferino Purple, Plate 26/3, page 26 (Wilson), with veins of petals near Solferino Purple, Plate 26/1, page 26 (Wilson); inside surface—near Solferino Purple, Plate 26/3, page 26 (Wilson), with veins of petals near Solferino Purple, Plate 26/1, page 26 (Wilson). 2–3 days open flower: Outer petals—outside surface—between Fuchsine Pink, Plate 627/3, page 78 (Wilson) and Fuchsine Pink, Plate 627/2, page 78 (Wilson), with veins of petals near Fuchsine Pink, Plate 627/3, page 78 (Wilson); inside surface—near Fuchsine Pink, Plate 627/3, page 78 (Wilson), with veins of petals near Fuchsine Pink, Plate 627/2, page 78 (Wilson). Inner petals—outside surface—between Fuchsine Pink, Plate 627/3, page 78 (Wilson) and Fuchsine Pink, Plate 627/2, page 78 (Wilson), with veins of petals near Fuchsine Pink, Plate 627/3, page 78 (Wilson); inside surface—near Fuchsine Pink, Plate 627/3, page 78 (Wilson), with veins of petals near Fuchsine Pink, Plate 627/2, page 78 (Wilson).

*General color effect.*—Newly opened flower—near Solferino Purple, Plate 26/3, page 26 (Wilson). 2–3 days open flower—near Fuchsine Pink, Plate 627/3, page 78 (Wilson).

*Behavior.*—Flowers persist on plant until they become old, and then drop off cleanly as entire flowers.

*Longevity.*—On bush in garden—from 4 to 7 days during February. Cut flowers grown outdoors and kept at room temperature—from 3 to 5 days.

*Reproductive Organs*

Stamens: Up to from 70 to 90 in number; from 5 to 20 mm. long; most with anthers; outer filaments united at base equal to from ¼ to ¾ of their length.

*Color of filament.*—From near Dawn Pink, Plate 523/3, page 137 (Wilson) at base to near Amber Yellow, Plate 505/3, page 132 (Wilson) at top of filament.

*Color of anthers.*—Newly opened flower—margins near Buttercup Yellow, Plate 5/1, page 5 (Wilson), with remainder near Straw Yellow, Plate 604/3, page 67 (Wilson). 2–3 days open flower—margins near Sudan Brown, Plate III (Ridgway), with remainder near Empire Yellow, Plate 603/3, page 66 (Wilson).

Pistils: 3 in number; from 1½ to 2½ cm. long.

*Color of style.*—Near Chartreuse Green, Plate 663/3, page 90 (Wilson).

*Color of stigma.*—Near Chartreuse Green, Plate 663, page 90 (Wilson).

Seed pods: Few; globular; from 20 to 25 mm. in diameter; surface usually covered with fine hairs; walls thick and fleshy. Color (mature)—near Sayal Brown, Plate XXIX (Ridgway).

Seeds: Usually one per pod; globular in shape.

I claim:

A new and distinct variety of Camellia plant, substantially as herein shown and described, characterized particularly as to novelty by the unique combination of a vigorous, upright and rather open habit of plant growth, attractive dark green glossy foliage of from small to medium size, a mid-season to late blooming period extending approximately two months or more in duration, a precocious blooming habit, a very floriferous habit, with the flowers borne laterally on most shoots as well as terminally, semi-double flowers of open form and varying from a rather formal, open-centered form to a very graceful, irregular and high-centered form, with several petals or petaloids intermixed with and partially covering the stamens, an attractive and distinctive light pink general color tonality of the flowers corresponding to near Solferino Purple, and a habit of the old flowers dropping cleanly as entire flowers.

No references cited.